United States Patent [19]
Warnick et al.

[11] Patent Number: 6,032,542
[45] Date of Patent: Mar. 7, 2000

[54] PREPRESSURED FORCE/PRESSURE SENSOR AND METHOD FOR THE FABRICATION THEREOF

[75] Inventors: Thomas Warnick, Wilmington; Boris Oreper, Newton, both of Mass.

[73] Assignee: Tekscan, Inc., South Boston, Mass.

[21] Appl. No.: 09/102,290

[22] Filed: Jun. 22, 1998

Related U.S. Application Data

[60] Provisional application No. 60/051,622, Jul. 7, 1997.
[51] Int. Cl.⁷ .................................................. G01L 1/04
[52] U.S. Cl. .................. 73/862.627; 73/862.474
[58] Field of Search ...................... 73/862.042, 862.044, 73/862.045, 862.046, 862.52, 862.627, 172, 862.473, 862.474, 862.68, 862.625, 777

[56] References Cited

U.S. PATENT DOCUMENTS 5,033,291   7/1991   Podoloff et al. ........................... 73/172

*Primary Examiner*—Joseph L. Felber
*Attorney, Agent, or Firm*—Wolf, Greenfield & Sacks, P.C.

[57] ABSTRACT

A pressure sensitive element or array is provided which includes at least one first conductor on a first substrate and at least one second conductor on a second substrate, with a first conductor and a second conductor intersecting adjacent to each other at a sensor point and a pressure sensitive material being between the first and second conductors at each such sensor point. A mechanism is also provided which applies a predetermined prepressure to the substrates at least at selected ones of the sensor points. The prepressure for a preferred embodiment is provided by joining the substrates with an air-tight seal around a periphery of at least the pressure point to which prepressure is to be applied and by creating a reduced pressure area between the substrates within the sealed periphery. For preferred embodiments, the reduced pressure is a substantial vacuum, causing substantially atmospheric pressure to be applied to the sensor points.

13 Claims, 1 Drawing Sheet

PREPRESSURED FORCE/PRESSURE SENSOR AND METHOD FOR THE FABRICATION THEREOF

RELATED APPLICATIONS

This application claims priority from provisional specification 60/051622 filed Jul. 7, 1997, the subject matter of which is incorporated herein by reference.

FIELD OF THE INVENTION

This invention relates to force/pressure sensor elements and arrays and more particularly to such elements/arrays which are prepressured to provide certain features and advantages and to two methods for the fabrication of such prepressured sensor elements/arrays.

BACKGROUND OF THE INVENTION

Pressure sensor elements can be utilized to provide an indication of ambient pressure in an environment or to provide a pressure measurement between two adjacent or contacting surfaces. Sensor arrays can also provide a profile of such pressure over a given area, including variations in such profile with time. Uses for such arrays include providing a dental occlusion profile for fitting crowns, bridges or false teeth, providing a foot pressure profile for fitting shoes or for orthopedic purposes, providing a pressure profile at a gasket to assure proper sealing at a joint and in numerous other medical, industrial, military and other applications.

One form of such pressure sensors utilizes a first substrate having at least one first conductor formed thereon, a second substrate having at least one second conductor formed thereon, and a pressure sensitive coating over the conductors on at least one of the substrates, the substrates being mounted such that the conductors on one substrate intersect conductors on the other substrate, with the variable resistant material therebetween, a pressure point being formed at each such intersection. Examples of such pressure sensitive arrays and of control circuitry for use therewith are shown in U.S. Pat. Nos. 4,856,993 issued Aug. 15, 1989, 5,033,291 issued Jul. 23, 1991 and 5,505,072 issued Apr. 9, 1996. In some applications, there may be only a single conductor on each substrate with only a single sensor point being formed. Such sensors are sometimes also referred to as "button sensors."

Sensors of the type indicated above have found wide application and provide significant advantages. However, such sensors also have certain limitation. First, since atmospheric pressure exists within such sensors, they are normally not capable of measuring pressures below atmospheric pressure (i.e. 14.7 psi) and thus have a relatively large force threshold.

Second, these sensors are subject to "drift" or "creep" when under load for a period of time. In particular, with a constant load, such increase tends to slow down over time, so that the longer a sensor is under load, the less drift occurs per unit of time. This drift can impact the reliability of readings.

Such sensors may also be subject to a hysteresis which results in the force/output profile being different when load is being increased than when load is being reduced. This can result in some inaccuracy and non-repeatability in readings which is undesirable. Repeatability can also be adversely affected when the pressure sensitive layers move with respect to one another between loadings of the sensor.

A need therefore exists for an improved sensor which overcomes the various problems indicated above.

SUMMARY OF THE INVENTION

In accordance with the above, this invention provides a pressure sensitive element which includes first and second nonconductive substrates positioned adjacent to each other. At least one first conductor is on the first substrate and at least one second conductor is on the second substrate, with a first conductor and a second conductor intersecting adjacent to each other at a sensor point. A pressure sensitive material is between the first and second conductors at each sensor point and a mechanism is provided which applies a predetermined prepressure to the substrates at least at selected ones of the sensor points. For preferred embodiments, the substrates are joined with an air-tight seal around a periphery of at least one of the sensor points and the predetermined pressure is achieved by a reduced air, low pressure area formed between the substrates within the sealed periphery. For a most preferred embodiment, the low pressure area is at substantial vacuum, causing substantially atmospheric pressure to be applied to each sensor point. For a sensor array, there are a spaced plurality of first conductors on the first substrate and a spaced plurality of second conductors on the second substrate, with a sensor point at each intersection where first and second conductors pass adjacent each other. For this embodiment, the air-tight seal is for a periphery around all of the sensor points. Substantially the same prepressure may be applied to all the pressure points or a predetermined prepressure profile may exist for the sensor points. The pressure sensitive material may be applied as a coating over at least one of the first electrodes and second electrodes.

Finally, for an alternative embodiment, the prepressure may be applied by a shrinkwrap around the sensor element(s).

For a preferred embodiment, a pressure sensitive element is fabricated by the steps of:

(a) providing a first substrate having at least one first conductor thereon, a second substrate with at least one second conductor thereon and a pressure sensitive material coated on at least one of the substrates over the at least one conductor thereon;

(b) assembling the substrates with at least one first conductor intersecting an adjacent second conductor at a sensor point, the pressure sensitive material being between conductors and in contact with the conductors at each sensor point;

(c) sealing a periphery around sensor points; and (d) creating a reduced pressure in the area between the substrates within the periphery.

For a preferred embodiment, during step (d), a substantial vacuum is created in the area between the substrates. For one embodiment of the invention, step (d) is performed by performing at least step (c), and preferably steps (a), (b) and (c), in a vacuum environment. For a second embodiment, step (d) includes the step of evacuating the area through an opening and sealing the opening. For still a third embodiment, step (d) includes the step performed during pressure sensing of actively pumping air from the area between the substrates.

The foregoing and other objects, features and advantages of the invention will be apparent from the following more particular description of preferred embodiments of the invention as illustrated in the accompanying drawings.

IN THE DRAWINGS

DETAILED DESCRIPTION

Figure 1:
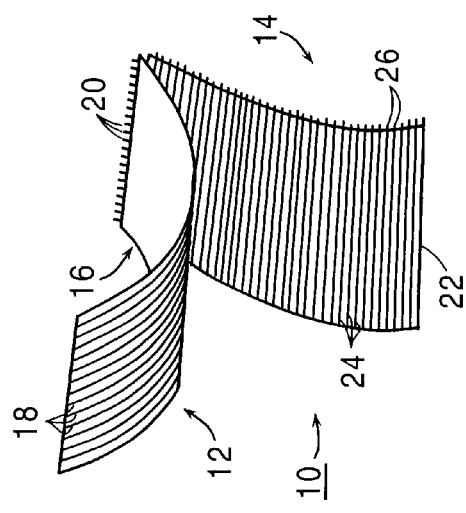
FIG. 1 is a perspective view of a partially assembled matrix sensor of a type which may be utilized in practicing the teachings of this invention.
Figure 2:
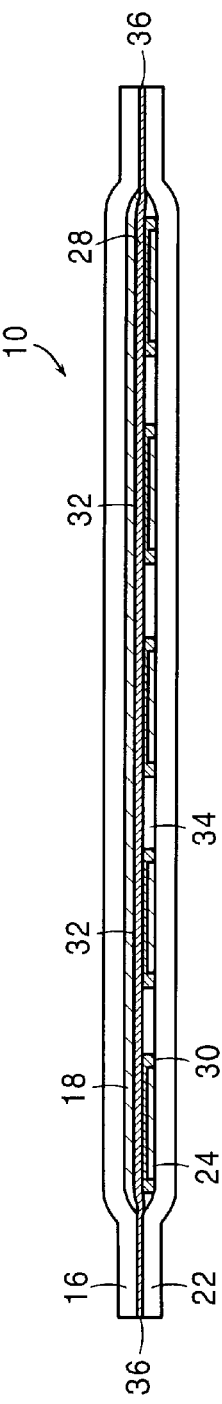
FIG. 2 is a side sectional view of a prior art sensor of the type shown in FIG. 1.

Referring to FIG. 1, a partially assembled sensor array 10 is shown which is formed of a first layer 12 and a second layer 14. Layer 12 consists of a flexible film or substrate 16, which may for example be of Mylar Plastic film or other suitable material, on the underside of which are formed a plurality of spaced conductors 18, each of which has an output terminal 20. Similarly, layer 14 consists of a substrate 22 on which are formed a plurality of spaced conductors 24, each of which has an output terminal 26. Referring to FIG. 2, it is seen that each conductor 18 is covered by a variable resistance coating 28 and that each conductor 24 is covered by a variable resistance coating 30. Materials suitable for such coatings are known in the art and at least some such materials are discussed in the before mentioned U.S. Pat. No. 4,856,993. From FIG. 2, it is also seen that when the layers 12 and 14 are assembled, there are a plurality of sensing cells or pressure points 32 where a conductor 18 and the variable resistance layer 28 thereon intersect with a conductor 24 and the variable resistance layer 30 thereon. However, between the pressure points 32, there are air gaps 34 which gaps are at atmospheric pressure and result in an atmospheric pressure within the sensor which must be overcome by any force applied thereto before such force can be detected. Substrates 16 and 22 are bonded at the peripheries of the sensor by an adhesive or other suitable bond 36, which bond is typically not a hermetic seal, meaning that air existing in gaps 34 may enter and leave these spaces as pressure is applied to the sensor.

The fact that there is atmospheric pressure in the gaps 34 of the sensor array shown in FIG. 2 means that at least atmospheric pressure has to be applied to the sensor before an increase in pressure is detected. This means that pressures below atmospheric pressure cannot be detected by the sensor, and in particular that the sensor cannot detect negative pressure in its environment. With no pressure on the sensor, the sensor is also subject to drift or creep and to hysteresis. In addition it is subject to relative motion between the pressure sensing layers. All of these characteristics may impact repeatability and accuracy.

Figure 3:
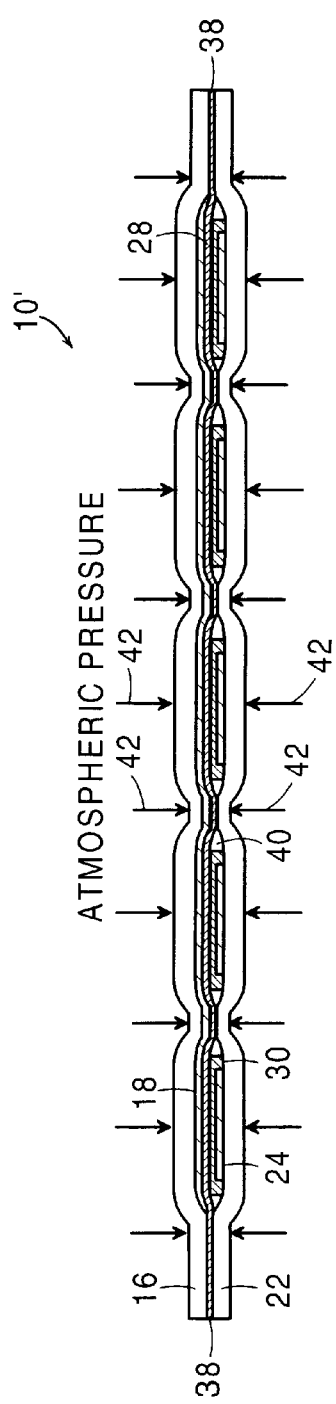
FIG. 3 is a side sectional view of a sensor in accordance with the teachings of this invention.

FIG. 3 shows a sensor 10' in accordance with the teachings with this invention which differs from that shown in FIG. 2 in that a hermetic seal 38 is utilized instead of the seal 36 and air is evacuated from the spaces 34 to provide a substantial vacuum at points 40 between sensing cells pressure points 32. The evacuation of sensor 10' results in an atmospheric prepressure 42 being applied to the sensor array. This atmospheric prepressure permits a decrease in ambient pressure in the environment to be detected by the sensor. Further, since the rate of drift or creep with increase in pressure decreases with respect to time, the longer the sensor is under load, the less drift occurs per unit of time. Therefore, if the sensor is under the constant load of atmospheric pressure, creep or drift is reduced to essentially zero. The force sensor threshold of an individual cell is also lowered which results in improved accuracy of both single cell sensors and multiple cell sensors, and thus an enhanced accuracy. The prepressure also reduces hysteresis for the variable resistance material, further enhancing accuracy and repeatability. Finally, since a known atmospheric pressure is being applied to this sensor under ambient conditions, this baseline pressure can be used for calibration purposed, thereby significantly simplifying the calibration process. A sensor with a number of significant advantages over prior art sensors for particular applications is thus provided.

Evacuation of air from the spaces 34 may be accomplished in a number of ways. One way of accomplishing this objective is to assemble layers 12 and 14 and form the seals 38 in a vacuum or a near vacuum environment. A second way to form the sensor arrays 10' is to initially form an array 10 with a hermetic seal 38 which array has an opening in one of the substrates 16, 22. Air is then evacuated from the spaces 34 by a vacuum pump connected to this opening and the opening is then hermetically sealed in manners known in the art. A final approach, which is somewhat more cumbersome, is to have an unsealed opening between the substrates which opening or openings is/are connected to a vacuum pump when the array is to be used. Other ways of forming the array 10' will be apparent to those skilled in the art.

While for the preferred embodiment, air is completely evacuated from the spaces 34 so that the sensor array 10' is under atmospheric prepressure, this is not a limitation on the invention, and less than all of the air may be evacuated from the spaces 34 so as to place the array under a selected known prepressure. Further, while for the preferred embodiment a seal is formed around the entire periphery of the array, one or more hermetic seals may be formed around selected portions of the array, with only a portion of the array being evacuated, or with different portions of the array being evacuated to different extents, to provide a selected prepressure profile for the array. In addition, while removing air from the array is the preferred way to prepressurize the array, other techniques known in the art could be utilized to achieve such prepressure. For example, the array 10 could be enclosed in a shrinkwrap plastic envelop, which is then heated and shrunk to prepressure the array. However, this technique is not believed to be as accurate, or to overcome as effectively all of the limitations of the prior art as the techniques previously described. Also, while an array of sensors has been shown in the figures, the teachings of this invention could be practiced for individual button sensors or button sensor arrays, where each button sensor could be individually evacuated. A single variable resistance layer 28, 30 could be utilized in some applications rather than two layers as shown. Finally, while a particular type of sensor array is shown in the figures, the teachings of this invention may be practiced utilizing other similar sensor arrays known in the art.

Thus, while the invention has been particularly shown and described above with reference to preferred embodiments, the foregoing and other changes in form and detail may be made therein by one skilled in the art without departing from the spirit and scope of the invention which is to be defined only by the appended claims.

We claim:

1. A pressure sensor element including:

first and second non-conductive substrates positioned adjacent to each other;

at least one first conductor on said first substrate and at least one second conductor on said second substrate, a said first conductor and a said second conductor intersecting adjacent to each other at a sensor point, said substrates being joined with an air-tight seal around a periphery of at least one sensor point; and a pressure sensitive material between said first and second conductors at each sensor point;

a reduced air, low pressure area being formed between said substrates within the sealed periphery resulting in a predetermined prepressure being applied to said substrates at said at least one sensor point.

2. A pressure sensor element as claimed in claim 1 wherein said low-pressure area is at substantial vacuum, causing substantially atmospheric pressure to be applied to each said at least one sensor point.

3. A pressure sensor element as claimed in claim 1 wherein there are a spaced plurality of at least one of first conductors on said first substrate and second conductors on said second substrate, there being a sensor point at each intersection where a first and second conductor pass adjacent each other, and wherein said air-tight seal is for a periphery around all said sensor points.

4. A pressure sensor element as claimed in claim 3 wherein substantially the same prepressure is applied to all the sensor points.

5. A pressure sensor element as claimed in claim 3 wherein a selected prepressure profile exists for said sensor points.

6. A pressure sensor element as claimed in claim 3 wherein said pressure sensitive material is applied as a coating over at least one of the first electrodes and the second electrodes.

7. A pressure sensor element including:

first and second non-conductive substrates positioned adjacent to each other;

at least one first conductor on said first substrate and at least one second conductor on said second substrate, a said first conductor and a said second conductor intersecting adjacent to each other at a sensor point;

a pressure sensitive material between said first and second conductors at each sensor point; and a shrinkwrap around said sensor element to apply prepressure thereto.

8. A method for fabricating a pressure sensor element including:

a) providing a first substrate having at least one first conductor thereon, a second substrate with at least one second conductor thereon and a pressure sensitive material coated on at least one of said substrates over the at least one conductor thereon;

b) assembling said substrates with at least one first conductor intersecting an adjacent second conductor at a sensor point, the pressure sensitive material being between conductors and in contact therewith at each sensor point;

c) sealing a periphery around sensor points; and d) creating a reduced pressure in the area between said substrates within said periphery.

9. A method as claimed in claim 8 wherein, during step (d), a substantial vacuum is created in said area between the substrates.

10. A method as claimed in claim 9 wherein step (d) is performed by performing steps (a), (b), and (c) in a vacuum environment.

11. A method as claimed in claim 9 wherein step (d) is performed by performing step (c) in a vacuum environment.

12. A method as claimed in claim 9 wherein step (d) includes the steps of evacuating said area through an opening, and sealing said opening.

13. A method as claimed in claim 11 wherein during step (c) there is at least one opening the sealing of said periphery; and wherein step (d) includes the step performed when said element is being used for pressure sensing of actively pumping air from said area through said at least one opening.

* * * * *